United States Patent [19]

DeRusha et al.

[11] Patent Number: 4,484,574
[45] Date of Patent: Nov. 27, 1984

[54] SELF-ROLLED FOAM TAPE WITHOUT RELEASE LAYER AND METHOD OF MAKING SAME

[75] Inventors: Mark A. DeRusha, El Toro; Thomas E. Schultz, Laguna Niguel; Stephen W. Luchio, Riverside, all of Calif.

[73] Assignee: Keene Corporation, New York, N.Y.

[21] Appl. No.: 573,854

[22] Filed: Jan. 25, 1984

[51] Int. Cl.³ .................. A61L 15/00; B32B 1/08; B32B 7/06; B32B 7/12
[52] U.S. Cl. .................... 128/156; 128/169; 128/170; 156/230; 156/238; 156/272.6; 156/324; 428/40; 428/214; 428/215; 428/314.4; 428/317.3; 428/343; 428/355; 428/906
[58] Field of Search .............. 428/40, 41, 42, 314.4, 428/314.8, 317.3, 317.7, 352, 355, 906, 213, 214, 215, 343; 128/156, 169, 170; 156/230, 238, 272.6, 324

[56] References Cited

U.S. PATENT DOCUMENTS

| | | | |
|---|---|---|---|
| 2,458,166 | 1/1949 | Homeyer, Jr. | 428/352 |
| 2,740,402 | 4/1956 | Scholl | 128/156 |
| 3,066,043 | 11/1962 | Hechtman et al. | 428/343 |
| 3,649,436 | 3/1972 | Buese | 428/317.3 |
| 4,021,001 | 5/1977 | Sproat | 428/317.7 |
| 4,163,822 | 8/1979 | Walter | 428/355 |
| 4,251,584 | 2/1981 | van Engelen et al. | 428/343 |
| 4,341,209 | 7/1982 | Schaar | 128/156 |
| 4,404,246 | 9/1983 | Charbonneau et al. | 428/317.3 |

FOREIGN PATENT DOCUMENTS

| | | | |
|---|---|---|---|
| 747341 | 11/1966 | Canada | 428/40 |
| 1232358 | 6/1969 | United Kingdom | 428/906 |

Primary Examiner—William J. Van Balen
Attorney, Agent, or Firm—Knobbe, Martens, Olson & Bear

[57] ABSTRACT

A pressure-sensitive tape having a closed-cell polymer foam backing strip and a pressure-sensitive adhesive is disclosed. The tape is formed into a roll so that the adhesive of one layer is in direct physical contact with the foam of the next layer, without the use of release paper or release coatings. The tape may be unwound without significantly disrupting either the adhesive layer or the foam layer. The foam is preferably a closed-cell cross-linked polyethylene copolymer and the adhesive is preferably a hypoallergenic acrylic-based adhesive.

18 Claims, 2 Drawing Figures

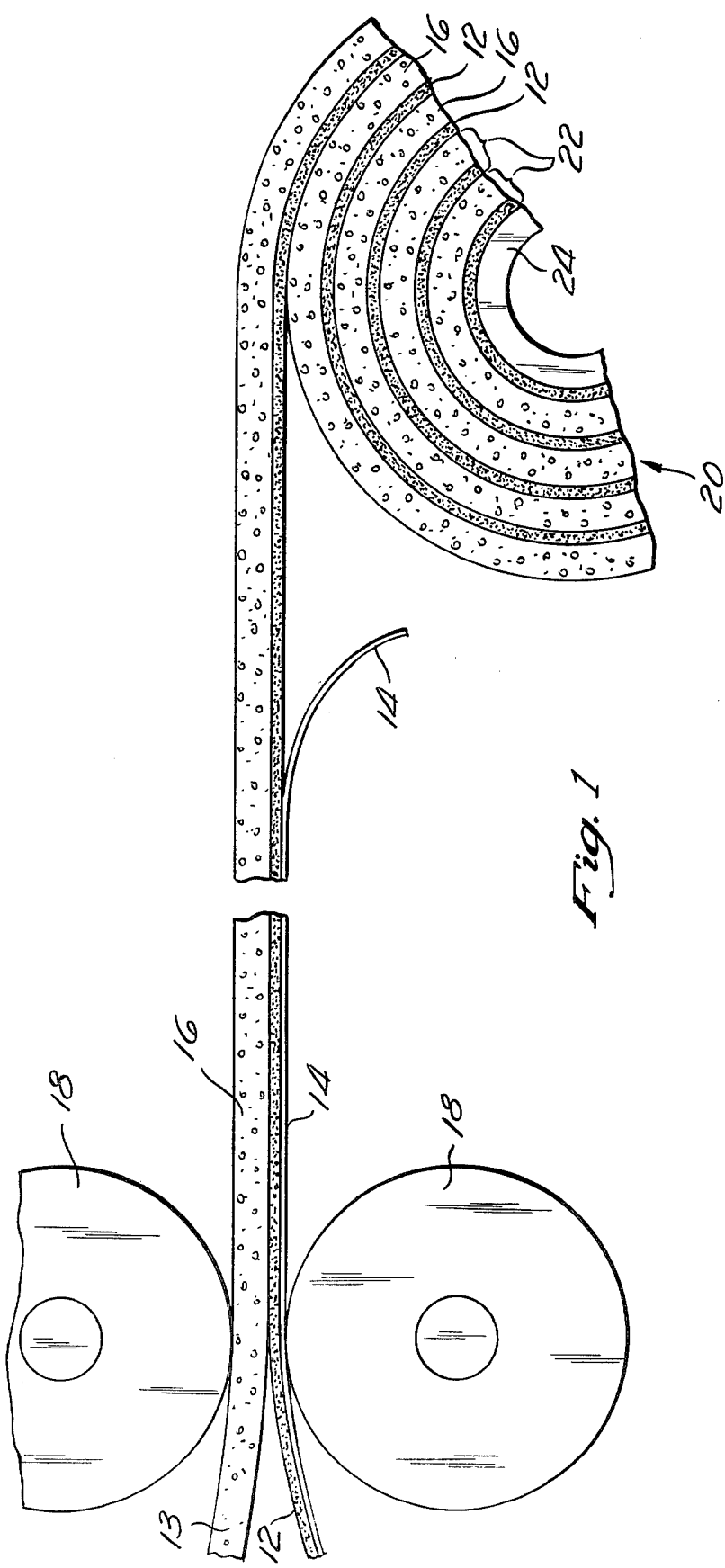
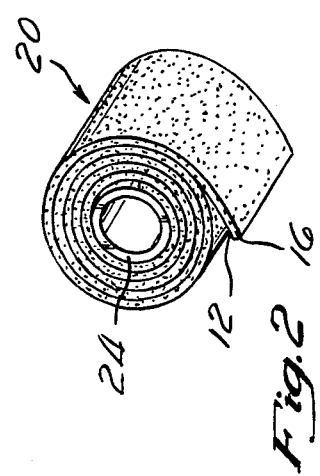

100 # SELF-ROLLED FOAM TAPE WITHOUT RELEASE LAYER AND METHOD OF MAKING SAME

BACKGROUND OF THE INVENTION

This invention relates to a foam tape which may be used, e.g., as a bandage hold down or an athletic wrap. In particular, the invention relates to a foam tape having a pressure-sensitive adhesive on one side, which can be formed into a roll and unrolled without disrupting the non-adhesive side of the tape or the adhesive and without the use of release paper or a release coating.

The use of adhesive tape in the treatment and prevention of sports injuries is well known. In general, the tape used is a cloth-backed tape, having a pressure-sensitive adhesive on one side thereof. The tape is generally porous and is supplied in roll form. This cloth-backed tape is particularly valuable for wrapping joints to prevent their movement. The tape has no appreciable stretch and, when wrapped several layers deep, it forms a hard, unyielding armour about the wrapped part.

However, conventional cloth-backed adhesive tape is not desirable for applications where limited movement of a joint is desired. Such tape can actually cut the skin when used for such applications, because of the unyielding nature of the material.

The use of stretchable foam material as a wrap for a limb is illustrated in U.S. Pat. No. 2,740,402 to W. M. Scholl. This patent discloses a bandage made of porous latex foam which may be coated with a pressure-sensitive adhesive. However, such a bandage would be unlikely to find wide-spread use in modern day training rooms, because it cannot be self-rolled. The patent recognizes that if the bandage is wrapped upon itself, the adhesive surface and possibly the non-adhesive surface would be disrupted in an attempt to unwrap the bandage. Accordingly, a release paper applied to the adhesive side of the bandage would be necessary in order to roll the tape for shipping. Release paper, however, would be a nuisance in the training room, and the bandage could not be applied directly from the roll to an object to be wrapped without removing the release paper.

An alternative to release paper is a release coating on the back side of the tape itself. Such coatings are illustrated in U.S. Pat. No. 2,458,166 to Homeyer, Jr., and U.S. Pat. No. 3,066,043 to Hechtman et al. The use of a release coating, however, is undesirable, both because of the added expense associated with applying the release layer to the tape in the manufacturing process and because there would be inadequate adhesion between successive layers of release-coated tape when used as an athletic wrap.

Schaar, in U.S. Pat. No. 4,341,209 discloses a backing sheet made of polyethylene foam for pressure-sensitive adhesive finger bandages. Finger bandages are, typically, supplied with a release paper covering the adhesive side of the bandage.

Furthermore, the use of closed-cell polymer foam adhesive strips for weather stripping and insulating is well known. However, to the Applicants' knowledge, none of the foregoing are capable of being self-rolled without the use of release paper.

SUMMARY OF THE INVENTION

In accordance with the present invention, there is provided a pressure-sensitive adhesive tape, comprising a web of closed-cell polymer foam material having a front side and a back side, the web being wound into a multilayered roll so that the front side is adjacent to the back side in successive windings. A layer of pressure-sensitive adhesive is located between and in direct contact with the adjacent front and back sides of the foam in the roll. The adhesive is releasable attached to the back side and permanently attached to the front side of the foam. Thus, upon unwinding, the pressure-sensitive adhesive coated front side of the tape separates relatively easily from the back side of the tape without disrupting either the adhesive layer or the back side of the foam, with which the adhesive on the front side of the foam was in direct physical contact.

In a preferred embodiment, the tape is a copolymer polyethylene foam having a hypoallergenic acrylic-based adhesive on one side. The thickness of the foam is between about 0.8 mm and about 6 mm, preferably between about 1 mm and about 3 mm, and most preferably about 1.6 mm (1/16 inches). The tape may be from about 12 mm to about 200 mm wide, preferably from about 20 mm to about 130 mm wide, and most preferably between about 24 mm and about 60 mm wide.

The present invention provides a lightweight self-frolled tape that provides support without restraint. It is particularly suitable for athletic applications where some flexibility of the wrapped member is desired. Unlike conventional adhesive tape, the present tape (which is capable of significant elongation) bends easily around complex or compound curves and does not cut the underlying flesh in use. The insulating properties of the tape permit retention of natural body heat.

The cellular structure of the tape also provides shock absorption properties. Injured members are prevented from touching other objects. The tape absorbs both sharp and dull impact, and rebounds for continuous absorption. The tape is waterproof and, because of its reversible self-winding nature, may be unwrapped (rather than cut) for removal.

BRIEF DESCRIPTION OF THE DRAWINGS

FIG. 1 is a schematic representation of the process of manufacturing the foam tape.

FIG. 2 is a perspective view of a roll of tape according to the invention.

DETAILED DESCRIPTION OF PREFERRED EMBODIMENTS

The two basic components of the tape of the present invention are the closed-cell polymer foam backing layer and the adhesive layer. The characteristics of the foam and the adhesive must be carefully matched, in order to provide a tape that may be self-rolled without significant damage to the foam or the adhesive layer upon unrolling.

The foam may be closed-cell polymer foam material having suitable characteristics, such as homopolymers and copolymers of polyethylene, polyurethane, or any of the vinyl-based polymers. The foam must be flexible and must be capable of being formed into sheets of 6 mm thickness or less having a tensile strength (in a foam of 2 mm thickness) of at least 100 g/cm width of tape. Elasticity is also an important property. The foam tape in the desired thickness must be capable of at least 50% elongation, and preferably at least 250%.

Foams containing migratory substances are generally unsuitable. Such substances tend to affect the properties of the adhesive. In addition, they reduce the shelf-life of the product and may not be suitable for prolonged contact with the skin. It is also desirable that the foam have an internal cellular structure and that the top and bottom surfaces of the foam exhibit continuous closed cell membranes. The membranes inhibit dirt or other substances from becoming ingrained into the foam and are also important in insuring that the self-rolled foam tape may be unrolled without significant disruption of the foam or the adhesive.

One preferred foam material is polyethylene homopolymer or copolymer. A suitable smooth-surfaced polyethylene copolymer foam sheet product is marketed by Voltek, Inc. under the trademark "VOLARA." VOLARA Type E foam is particularly preferred. Type E VOLARA is closed-cell foamed polyethylene-vinyl acetate copolymer that has been irradiation cross-linked. Its closed-cell structure is often called "fine celled". In a 1.6 mm thickness, it has a tensile strength of 620 g/cm width in tape form and may be elongated 250%. VOLARA is hypoallergenic and does not contain migratory plasticizers. Another suitable foam is a cross-linked polyethylene marketed by the Frelen Corporation under the trademark FRELEN XLPE. Closed-cell, foams, such as those marketed by 3-M Corporation, Compo Industries, E.A.R. Corporation, and Monosol, are also suitable, as are Uniroyal's polyvinylchloride-nitrile rubber foams.

The adhesive must be capable of adhering securely to one side of the foam and yet, when cured, must releasably adhere to the other side of the foam. This property permits the tape according to the invention to be self-rolled without the use of release paper or release coatings so that the tape may be self-rolled. Certain acrylic, rubber, urethane, and silicone based adhesives are suitable. A suitable adhesive will have an adhesive shear strengh of, for example, 1 kg/6.25 cm$^2$ for 167 hours. The viscosity of the adhesive prior to application to the foam will be 500–20,000 centipoises. An even more important determinant of suitability is the cohesive strength of the adhesive. A relatively "hard" adhesive is required if the tape is to be reversibly self-rolled. The adhesive should have a peel strength (as measured by Pressure Sensitive Tape Council adhesion test method 1 (PSTC-1) of 250 g/cm width to 850 g/cm width at 1 mil adhesive thickness, and preferably about 550 g/cm. Crosslinked acrylic adhesives are particularly preferred. It is highly desirable that the adhesive be hypoallergenic. One suitable acrylic-based adhesive is National Adhesives DURO-TAK TM 80-1054. Another is Monsanto 737. Still another is Ashland's AROSET TM 1910. The adhesive is preferably dispersed in an aqueous or hydrocarbon vehicle.

FIG. 1 illustrates in part the preferred process for making the foam tape according to the present invention. A layer of suitable adhesive 12 is spread on a release paper 14 by any suitable apparatus, such as a knife over a roll, a knife over a fixed rod or bed, or a Meyer rod. Any suitable release paper may be used, although a doublesided silicone-treated release paper such as H. P. Smith 8054 POLYSLIK TM is preferred. The vehicle is then flashed off by the application of heat to leave a uniform layer of adhesive 12 on the release paper 14. This is preferably done in a zoned air-circulating oven having a final temperature of between about 95° C. and about 135° C., and preferably about 120° C. The adhesive layer is between 0.5 and 2.2 mils thick, and is preferably about 1 mil thick. The adhesive-coated side of release paper 14 is then mated with the front side 13 of a sheet of foam 16 between the pinch rollers 18 at ambient temperature. Optionally, the foam has been previously treated by a conventional corona discharge process ($\leq$46 dyne) to enhance adhesive bonding. A three-layer sandwich of foam 16, adhesive 12, and release paper 14 results. In a preferred embodiment the foam, adhesive, and release paper sandwich is self-rolled and stored for a period of time sufficient to allow the adhesive to set, generally for a minimum of 24 hours. The foam, adhesive and release paper are then unrolled.

As is shown in FIG. 1, the release paper is removed, leaving the adhesive layer 12 permanently affixed to the foam 16. The resulting pressure-sensitive foam tape is then slit to the desired width and self-rolled (without tension) into a multi-layered roll 20 having a plurality of layers 22. Each layer 22 comprises a layer of foam 16 and a layer of adhesive 12. Except for the innermost layer, each layer of adhesive 12 is disposed between two layers of foam 16. In the roll, adhesive 12 is permanently affixed to the front side 13 of the adjacent covering layer of foam and is releasably adhered to the back side 24 of the supporting layer of foam.

The completed product is illustrated in FIG. 2, which is a roll 20 of pressure-sensitive adhesive tape having a foam layer 16 and an adhesive layer 12, in which the adhesive side of each layer is in direct physical contact with the foam material of the underlying layer. The roll is formed around a cylindrical core 24. Because no release coatings or backing papers are used, the adhesive side of each layer is releasably attached directly to the form of the underlying tape.

The tape of the present invention may be used in several ways in industrial, veterinary, athletic, and medical applications. For example, the tape may be used as a protective padding over sterile dressings. It is useful as a wrap about the limb of a mammal to prevent and treat injuries. It may be used to pad fingers, foreheads, bruises, and tendons. It may also be used to pad splints and casts externally, to minimize the effect of jolts and shocks, and may even be used in certain circumstances as a soft cast for a broken bone. Because the tape can be reversably self-rolled, multiple wrappings of tape may be removed without cutting the tape.

The tape may also be applied to any surface to provide padding. Grips, handles, and sharp surfaces may advantageously be covered. It also has utility as a metal-to-metal gasket.

EXAMPLE 1

A sheet of VOLARA type E polyethylene copolymer foam approximately 140 cm wide and 1.6 mm thick is conventionally treated with a 50 dyne corona discharge. A layer of Ashland's AROSET 1910 adhesive is applied with a knife to a sheet of double-sided silicone treated release paper. The release paper and adhesive then pass through a zoned, heated, air-circulating oven to remove the hydrocarbon vehicle from the adhesive. The final oven temperature is 120° C. The adhesive-coated side of the release paper is next mated with the corona-treated side of the foam. The foam-adhesive-release paper sandwich is then self-rolled. After 24 hours the release paper is removed and the tape is cut into 50 mm wide strips and self-wound on a polyethylene core. The resulting tape is disposed on the roll so that the adhesive side of one layer of tape is in direct physical contact with the foam backing of the adjacent layer. The foam tape may be unwound without significant disruption of either the adhesive layer or the foam layer. No significant amount of adhesive remains on the foam side of the tape. The resulting tape is strong, light, shock-absorbant and adheres strongly but releasably to virtually any clean, dry surface including glass, metal, fabric, plaster casts, and human skin.

EXAMPLE 2

A strip of tape 50 mm wide, prepared according to Example 1, is wrapped around the limb of a mammal and over an ankle joint in multiple overlapping layers. The resulting wrap permits some movement of the ankle while providing support. The wrapping also cushions the wrapped portion against blows and significantly reduces the possibility of bruising and cartilage, tendon, and ligament injury.

Although this invention has been described in terms of certain preferred embodiments, other embodiments that are apparent to those of ordinary skill in the art are also within the scope of this invention. Accordingly, the scope of the invention is intended to be limited only by the appended claims.

What is claimed is:

1. A pressure-sensitive adhesive tape, comprising:
   a web of closed-cell polymer foam material having a front side and a back side;
   said web being wound into a multi-layered roll so that said front side is adjacent to said back side in successive windings;
   a layer of pressure-sensitive adhesive disposed between and in direct contact with said adjacent front and back sides of said foam;
   said adhesive being releasably attached to said back side and permanently attached to said front side.

2. The tape of claim 1, wherein said adhesive is hypoallergenic.

3. The tape of claim 2, wherein said adhesive is an acrylic adhesive.

4. The tape of claim 2, wherein said polymer is polythylene.

5. The tape of claim 4, wherein said foam is a polyethylene copolymer and said front and said back sides are substantially smooth.

6. The tape of claim 4, having a thickness of between about 0.8 mm and about 6 mm and a width of between about 12 mm and about 200 mm.

7. The tape of claim 6, wherein said adhesive is between about 0.5 and about 2.2 mils thick and has a PSTC-1 peel strength between about 250 g/cm width and about 850 g/cm width at 1 mil adhesive thickness.

8. The tape of claim 6, wherein said adhesive has a PSTC-1 peel strength of about 550 g/cm width at 1 mil adhesive thickness.

9. The tape of claim 4, having a thickness of between about 1 mm and about 3 mm and a width of between about 20 mm and 200 mm.

10. An article of manufacture, comprising
    a web of closed-cell polyethylene foam material having a front side and a back side;
    a layer of pressure-sensitive adhesive permanently affixed to said front side;
    said adhesive layer being releasably attachable to said back side of said foam to permit the front side of one part of said web to be adhesively attached to the back side of another part of said web and then separated without substantially disrupting said back side.

11. The article of claim 10, wherein said adhesive is hypoallergenic.

12. The article of claim 10, wherein said adhesive is between about 0.5 and about 2.2 mils thick and has a PSTC-1 peel strength between about 250 g/cm width and about 850 g/cm width at 1 mil adhesive thickness.

13. The article of claim 12, wherein said adhesive has a PSTC-1 peel strength of about 550 g/cm width at 1 mil adhesive thickness.

14. The article of claim 11, wherein said polymer is polyethylene.

15. The article of claim 11, wherein said adhesive is an acrylic adhesive.

16. The article of claim 10, wherein said article is formed into a roll having successive layers and the adhesive of one layer is directly and releasably adhered to the foam of another layer.

17. The article of claim 11, wherein said article is a bandage applied to a limb of a mammal in overlapping layers, the adhesive of one layer being in direct physical contact with the foam of an adjacent layer.

18. A process for making a self-rolled pressure-sensitive adhesive foam tape, comprising the steps of:
    subjecting a closed-cell polymer foam web to corona discharge;
    applying a layer of pressure-sensitive adhesive to a release paper;
    mating the foam web to the adhesive;
    forming the foam web, the adhesive, and the release paper into a multi-layered roll;
    unrolling the web, the adhesive, and the release paper;
    removing the release paper, leaving a pressure-sensitive adhesive tape having a foam backing side and an adhesive side; and
    self-rolling the pressure-sensitive adhesive tape into a multi-layered roll so that the adhesive side of one layer is in direct physical contact with the foam side of an adjoining layer.

* * * * *